United States Patent [19]

Kennedy

[11] Patent Number: 4,581,346

[45] Date of Patent: Apr. 8, 1986

[54] MACROLIDE DERIVATIVES

[75] Inventor: Joseph H. Kennedy, Clarks Hill, Ind.

[73] Assignee: Eli Lilly and Company, Indianapolis, Ind.

[21] Appl. No.: 630,154

[22] Filed: Jul. 12, 1984

[51] Int. Cl.[4] .................. A61K 31/71; C07H 15/08
[52] U.S. Cl. .................................. 514/30; 536/7.1
[58] Field of Search .............. 536/7.1; 424/180; 514/30

[56] References Cited

U.S. PATENT DOCUMENTS

| | | | |
|---|---|---|---|
| 3,178,341 | 4/1965 | Hamill et al. | 167/65 |
| 3,326,759 | 7/1962 | Hamill et al. | 167/65 |
| 4,345,069 | 8/1982 | Sakakibara et al. | 536/7.1 |
| 4,385,116 | 5/1983 | Baltz et al. | 435/76 |

OTHER PUBLICATIONS

Matsubara et al., "Chemical Transformation of Tylosin, a 16-Membered Macrolide, and Its Structure-Activity Relationship," Chem. Pharm. Bull. 30(1) 97–100 (1982).

Primary Examiner—Johnnie R. Brown
Assistant Examiner—Elli Peselev
Attorney, Agent, or Firm—Nancy J. Harrison; Arthur R. Whale

[57] ABSTRACT

C-8, 20-cyclo-derivatives of the macrolide antibiotics tylosin, desmycosin, macrocin, lactenocin, 2'''-O-demethylmacrocin and 2''-O-demethyllactenocin, which inhibit pathogenic bacteria, especially gram-positive bacteria, and Mycoplasma species, and pharmaceutical compositions thereof, are provided.

17 Claims, No Drawings

MACROLIDE DERIVATIVES

SUMMARY OF THE INVENTION

This invention relates to C-8,20-cyclo-macrolide derivatives having formula 1

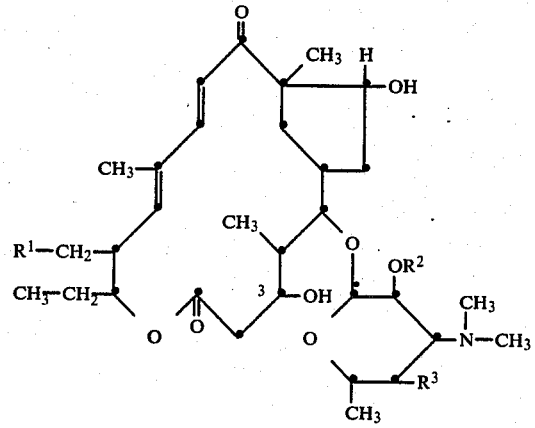

wherein
$R^1$ is

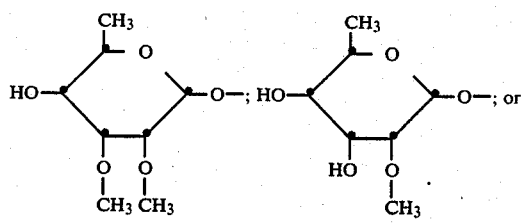

$R^2$ is hydrogen, optionally substituted $C_1$–$C_5$-alkanoyl or optionally substituted benzoyl, phenylacetyl or phenylpropionyl;

$R^3$ is hydrogen; hydroxy; optionally substituted $C_1$–$C_5$-alkanoyloxy; optionally substituted benzoyloxy, phenylacetoxy or phenoxyacetoxy; or

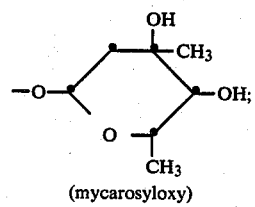
(mycarosyloxy)

and to the acid addition salts of these compounds.

The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of C-8,20-cyclo-derivatives of the macrolide antibiotics tylosin, desmycosin, macrocin, lactenocin, 2'''-O-demethylmacrocin (DOMM) and 2''-O-demethyllactenocin (DOML) and to the acid addition salts of these derivatives. This invention also relates to methods of treating certain infections with, methods of promoting growth in animals with, and pharmaceutical compositions comprising the specified derivatives or their pharmaceutically acceptable acid addition salts.

New antibiotics are continually in demand for treating diseases in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for these new antibiotics.

This invention relates to the discovery that antibiotics such as tylosin, when allowed to stand in an aqueous solution at a basic pH, will form the corresponding formula 1 derivative and that the derivatives also have useful antibacterial properties.

The novel macrolides of this invention are compounds of formula 1:

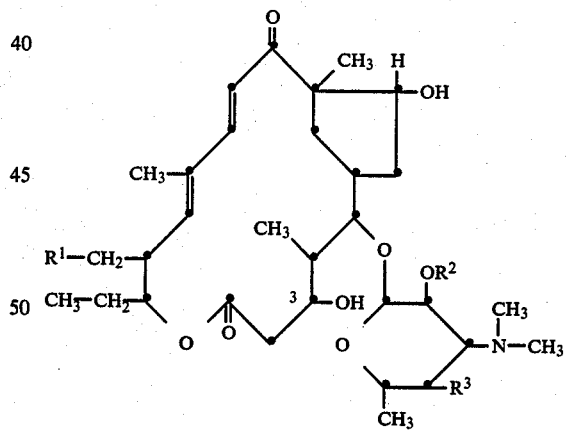

wherein
$R^1$ is

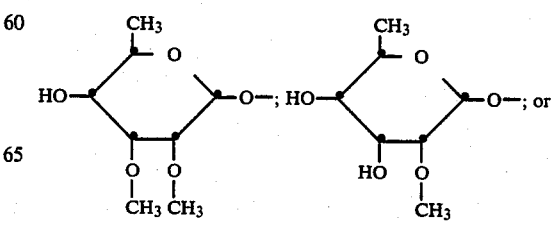

-continued

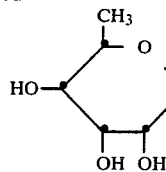

$R^2$ is hydrogen, optionally substituted $C_1$–$C_5$-alkanoyl or optionally substituted benzoyl, phenylacetyl or phenylpropionyl;

$R^3$ is hydrogen; hydroxy; optionally substituted $C_1$–$C_5$-alkanoyloxy; optionally substituted benzoyloxy, phenylacetoxy or phenoxyacetoxy; or

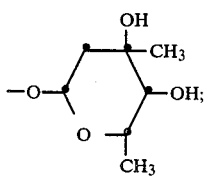

and the acid addition salts of these compounds.

Although no stereochemical assignments are indicated in the structures given herein, the stereochemistry is identical to that of the antibiotics from which the compounds are prepared, e.g. tylosin.

The term "$C_1$–$C_5$-alkanoyl" as used herein refers to an acyl moiety derived from a carboxylic acid containing from one to five carbon atoms. When optionally substituted, the alkyl group can bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups. The term "$C_1$–$C_5$-alkanoyloxy" refers to the corresponding acyloxy moiety.

The terms "optionally substituted benzoyl, phenylacetyl or phenylpropionyl" and "optionally substituted benzoyloxy, phenylacetoxy or phenxoyacetoxy" mean that the phenyl portion of the moiety is optionally substituted by from one to five halo or methyl groups or by from one to two methoxyl, nitro or hydroxyl groups.

The C-8,20-cyclo-macrolide derivatives of this invention are prepared from the group of macrolide antibiotics which includes tylosin, desmycosin, macrocin, 2'''-O-demethylmacrocin (DOMM), lactenocin, and 2''-O-demethyllactenocin (DOML).

Tylosin and desmycosin are described by R. L. Hamill et al. in U.S. Pat. No. 3,178,341, issued Apr. 13, 1965. Macrocin and lactenocin are described by Hamill et al. in U.S. Pat. No. 3,326,759, issued June 20, 1967. DOMM and DOML are antibiotics described by R. H. Baltz et al. in U.S. Pat. No. 4,385,116, issued May 24, 1983. The structures of these antibiotics are shown in formulas 2–7:

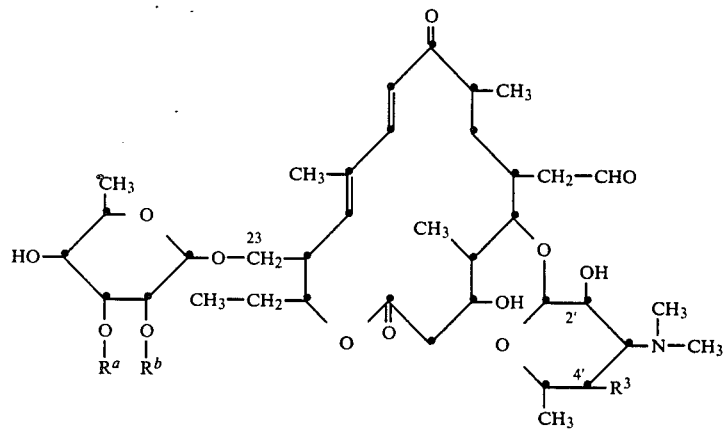

|  | $R^a$ | $R^b$ | $R^3$ |
|---|---|---|---|
| 2 (tylosin): | —CH₃ | —CH₃ | —O—mycarosyl |
| 3 (desmycosin): | —CH₃ | —CH₃ | —OH |
| 4 (macrocin): | H | —CH₃ | —O—mycarosyl |
| 5 (lactenocin): | H | —CH₃ | —OH |
| 6 (DOMM): | H | H | —O—mycarosyl |
| 7 (DOML): | H | H | —OH |

The C-8,20-cyclo-macrolide derivatives are prepared by permitting the starting antibiotic to stand in an aqueous solution having a pH greater than 7. A pH in the range of from about 8.5 to about 9.5 is preferred. The product compounds form very slowly at room temperature (about 8 months), but form more rapidly at higher temperatures. Reaction temperatures in the range of from about 40° to about 80° C. are recommended.

Once formed, the formula 1 compounds can be isolated by various procedures, such as extractive or chromatographic methods. Because the products are very similar to the starting antibiotics, high performance liquid chromatography (HPLC) is particularly suitable for separating the formula 1 compounds. Representative processes are illustrated in the Examples, but other suitable procedures can be devised.

The C-8,20-cyclo-derivatives of desmycosin, lactenocin and DOML can also be prepared by acidic hydrolysis of mycarose from the corresponding derivatives of tylosin, macrocin and DOMM, respectively. Procedures for this are well known (see, for example, U.S. Pat. No. 4,321,362).

The C-8,20-cyclo-4'-deoxy derivatives of this invention, i.e. the compounds of formula 1 wherein $R^3$=H, can be prepared by procedures analogous to those described supra, using the 4'-deoxy-derivative of compounds 3, 5 or 7 as starting materials. These can be prepared via procedures outlined in *J. Antibiotics* 34, 1381–1384 (1981).

The ester derivatives of this invention are prepared by esterifying the appropriate C-8,20-cyclo-derivative on the 2'- or 2' and 4'-hydroxyl groups by treatment with acylating agents, using standard methods well exemplified in the art. The preparation of 2'-O-ester derivatives is accomplished by procedures similar to those described by Baltz et al. in U.S. Pat. Nos. 4,321,361 and 4,321,362. 2',4'-Di-O-ester derivatives may be prepared using procedures analogous to those described by Herbert A. Kirst in U.S. Pat. No. 4,401,660, issued Aug. 30, 1983.

The C-8,20-cyclo-derivatives of this invention form salts, particularly acid addition salts. These acid addition salts are also useful as antibiotics and are a part of this invention. In another aspect, such salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

Illustrative derivatives of this invention include the compounds listed in Table I.

TABLE I

Illustrative Formula 1 Derivatives

| Compound No. | $R^1$ | $R^2$ | $R^3$ |
|---|---|---|---|
| 1 | (CH3, HO, O, O-, O, O, CH3, CH3 ring) | H | mycarosyloxy |
| 2 | " | " | OH |
| 3 | " | " | H |
| 4 | (CH3, HO, O, O-, O, O, H, CH3 ring) | " | mycarosyloxy |
| 5 | " | " | OH |
| 6 | (CH3, HO, O, O-, O, O, H, H ring) | " | mycarosyloxy |
| 7 | " | " | OH |

The formula 1 compounds inhibit the growth of certain pathogenic bacteria. The minimal inhibitory concentrations (MIC's) at which the tylosin derivative (formula 1 compound wherein

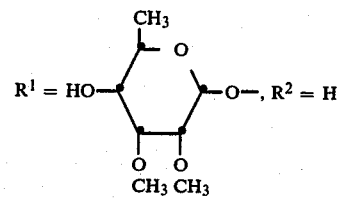

$R^1 = $ HO-[ring], $R^2 = $ H and $R^3 = $ mycarosyloxy) inhibits certain bacteria are given in Table II. The MIC's in Table II were determined by standard agar-dilution assays.

TABLE II

| Antibacterial Activity of 8,20-Cyclo-Tylosin | |
|---|---|
| Test Organism | MIC (mcg/ml) |
| Staphylococcus aureus X1.1 | 1 |
| Staphylococcus aureus V41[a] | 2 |
| Staphylococcus aureus X400[b] | 2 |
| Staphylococcus aureus S13E | 2 |
| Staphylococcus epidermidis EPI1 | 1 |
| Staphylococcus epidermidis EPI2 | 0.5 |
| Streptococcus pyogenes C203 | 1 |
| Streptococcus pneumoniae Park I | 2 |
| Streptococcus Group D X66 | 32 |
| Streptococcus Group D 9960 | 32 |
| Haemophilus influenzae C.L.[c] | 128 |
| Haemophilus influenzae 76[d] | 128 |
| Escherichia coli N10 | >128 |
| Escherichia coli EC14 | >128 |
| Escherichia coli TEM | >128 |

[a]Penicillin-resistant strain
[b]Methicillin-resistant strain
[c]Ampicillin-sensitive strain
[d]Ampicillin-resistant strain This invention also relates to methods of controlling infections caused by bacterial and mycoplasmal species which are sensitive to the formula 1 compounds. In carrying out these methods, an effective amount of a formula 1 compound is administered parenterally or orally to a warm-blooded animal. The compounds can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.5 to about 50 mg/kg. The dose required for oral administration will generally be in the range of from 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of infections caused by bacteria and Mycoplasma species which are sensitive to the formula 1 compounds. These compositions comprise a formula 1 compound together with a suitable vehicle. Compositions may be formulated for parenteral or oral administration by methods recognized in the pharmaceutical art.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a formula 1 compound.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following example is provided.

EXAMPLE 1

Preparation of 8,20-Cyclo-tylosin

This compound is prepared by permitting Tylan 200 (a preparation of tylosin in 50% propylene glycol and 4% benzyl alcohol in water at a concentration of 200 mg/ml) to stand for from 8 to 22 months at room temperature. The procedure can be accelerated by increasing the temperature to about 60° C. for 10 days and adjusting the pH to 9.0. 8,20-Cyclo-tylosin is detectable as 4-5% of the product under these conditions, whereas it would take about 12 months at room temperature to form this much. The pH of the solution should be 7 or above to minimize formation of other by-products.

8,20-Cyclo-tylosin is isolated by high performance liquid chromatography (HPLC), using the following conditions and procedure:

Instrumental Conditions

Column: 21-mm i.d.×25-cm Zorbax C8 (DuPont Inst.)
Column Eluant: acetonitrile:0.25 M $NaClO_4$ (2:3), pH to 2.5 with HCl
Flow Rate: 14 ml/min
Injection: 0.5 to 0.7 ml, using 1-ml fixed volume loop
Detector: UV at 300 nm

Procedure

Sample Preparation: Add the solution (1 ml) to acetonitrile (4 ml). Sample concentration is approximately 40 mg/ml. Inject as much sample as possible so that the product peak may be distinguished from tylosin. 20 mg to 30 mg of sample may be injected on the column with adequate resolution from tylosin.

Collect the desired peak from each injection. Adjust the pH of the collected aliquot to 9.0, using 0.5 N KOH, and extract with chloroform. Filter the chloroform solution through anhydrous sodium sulfate and evaporate to dryness.

Since compound 1 elutes so close to tylosin, it was necessary to repeat the procedure on combined aliquots from the first isolation. Residues from two such purifications were dissolved in amyl acetate (10 ml). Compound 1 was extracted from the amyl acetate solution, using two 10-ml aliquots of pH 4 potassium acetate buffer. This extraction into the acetate buffer was necessary to remove hydrocarbon residues from the HPLC column. The pH of the acetate buffer was adjusted to 9.0, and compound 1 was extracted into chloroform. The chloroform extracts from the two runs were evaporated to give 8,20-cyclo-tylosin (compound 1), having a purity of 93% and 86%, respectively.

Identification

The field desorption mass spectrum of compound 1 has a protonated molecular ion at 916, as does tylosin. The UV spectrum of 1 shows that the ketodiene chromophore is still intact. In the $^1H$ NMR spectrum of 1 in $CDCl_3$, the aldehyde proton normally present at 9.6 ppm is missing. A methine triplet is present at 4.08 ppm and is coupled to a resonance(s) at 1.66 ppm. The spectrum in pyridine-$d_5$ shows a new methyl singlet and the loss of one methyl doublet. Decoupling experiments show that the new methyl singlet is C-21.

The $^{13}C$ NMR spectrum of compound 1 compared to that of tylosin is shown in Table III.

TABLE III $^{13}C$ NMR Comparison of Tylosin and its Aldol Product

| Position | Tylosin | Compound 1 |
|----------|---------|------------|
| 1        | 173.92  | 174.60     |
| 2        | 39.41   | 39.15      |
| 3        | 71.76   | 72.00      |
| 4        | 45.05   | 43.06      |
| 5        | 81.23   | 80.15      |
| 6        | 31.93   | 37.33      |
| 7        | 32.77   | 34.71      |
| 8        | 40.28   | 58.18      |
| 9        | 203.15  | 205.45     |
| 10       | 118.60  | 122.49     |
| 11       | 148.13  | 144.93     |
| 12       | 134.87  | 135.02     |

TABLE III-continued
$^{13}C$ NMR Comparison of Tylosin and its Aldol Product

| Position | Tylosin | Compound 1 |
|---|---|---|
| 13 | 142.36 | 139.49 |
| 14 | 44.71 | 44.71 |
| 15 | 75.16 | 75.47 |
| 16 | 25.39 | 25.63 |
| 17 | 9.67 | 9.57 |
| 18 | 9.04 | 9.57 |
| 19 | 43.74 | 37.07 |
| 20 | 203.00 | 73.47 |
| 21 | 17.39 | 17.30 |
| 22 | 12.99 | 12.83 |
| 23 | 69.06 | 69.44 |
| 1' | 103.72 | 104.02 |
| 2' | 67.89 | 67.59 |
| 3' | 68.75 | 68.91 |
| 4' | 75.08 | 75.35 |
| 5' | 73.15 | 73.24 |
| 6' | 19.02 | 19.13 |
| NMe$_2$ | 41.97 | 42.01 |
| 1'' | 96.50 | 96.64 |
| 2'' | 40.92 | 41.04 |
| 3'' | 69.49 | 69.15 |
| 4'' | 76.42 | 76.59 |
| 5'' | 66.03 | 66.12 |
| 6'' | 18.25 | 18.25 |
| 7'' | 25.39 | 25.42 |
| 1''' | 101.07 | 101.14 |
| 2''' | 81.89 | 82.15 |
| 3''' | 79.83 | 79.85 |
| 4''' | 72.71 | 72.77 |
| 5''' | 70.56 | 70.71 |
| 6''' | 17.76 | 17.78 |
| 2'''—OMe | 59.69 | 59.62 |
| 3'''—OMe | 61.76 | 61.71 |

EXAMPLE 2

Analytical HPLC Conditions[a]

Compound 1 is conveniently separated from tylosin using the following HPLC system:
Column: 4.6 mm I.D. ×25 cm Zorbax C8
Eluant: 23% acetonitrile, 19% tetrahydrofuran and 58% ion pair solution (250 mg pentane sulfonic acid per liter of 1% acetic acid in water)
Flow rate: 2.5 ml/min
Temp.: 50° C.
Retention times: 16.27 min (compound 1), 18.00 min (tylosin).

[a]See also Kennedy, *J. Chromatography* 281, 288-292 (1983)

I claim:

1. A macrolide compound of the formula

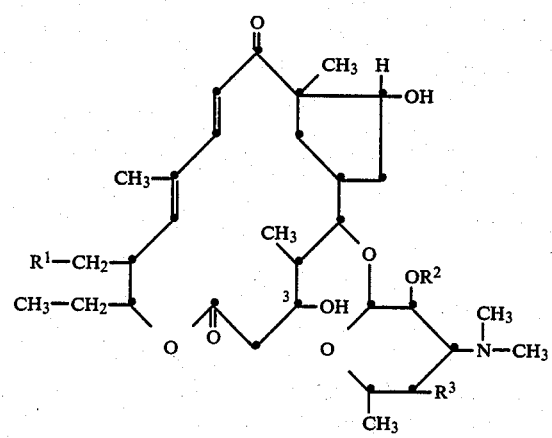

wherein
$R^1$ is

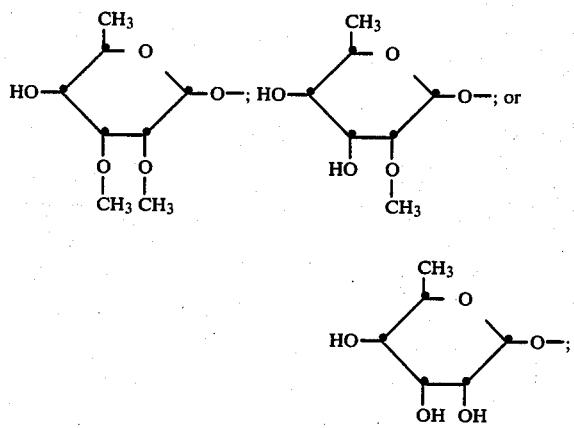

$R^2$ is hydrogen; $C_1$-$C_5$-alkanoyl; $C_1$-$C_5$-alkanoyl having from one to three halo substituents; benzoyl, phenylacetyl or phenylpropionyl or benzoyl, phenylacetyl or phenylpropionyl having from one to five halo or methyl or from one to two methoxyl, nitro or hydroxyl groups on the phenyl ring;

$R^3$ is hydrogen; hydroxy; $C_1$-$C_5$-alkanoyloxy; $C_1$-$C_5$-alkanoyloxy having from one to three halo substituents; benzoyloxy, phenylacetoxy or phenoxyacetoxy; or benzoyloxy, phenylacetoxy or phenoxyacetoxy having from one to five halo or methyl or from one to two methoxyl, nitro or hydroxyl groups on the phenyl ring; or

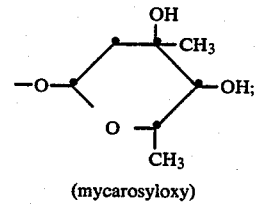

(mycarosyloxy)

and its pharmaceutically acceptable acid addition salts.

2. A compound of claim 1 wherein $R^1$ is

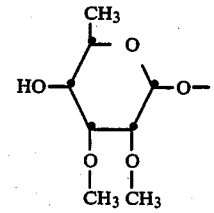

3. A compound of claim 2 wherein $R^3$ is mycarosyloxy.

4. A compound of claim 2 wherein $R^3$ is hydroxy.

5. A compound of claim 1 wherein $R^1$ is

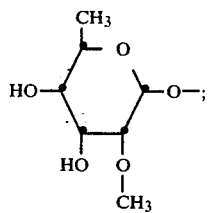

6. A compound of claim 1 wherein $R^1$ is

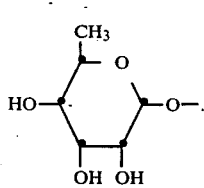

7. A composition useful for the treatment of susceptible bacterial infections comprising an effective amount of a compound of claim 1 or a pharmaceutically acceptable acid addition salt thereof and a suitable pharmaceutical vehicle.

8. A composition useful for the treatment of susceptible bacterial infections comprising an effective amount of a compound of claim 2 or a pharmaceutically acceptable acid addition salt thereof and a suitable pharmaceutical vehicle.

9. A composition useful for the treatment of susceptible bacterial infections comprising an effective amount of a compound of claim 3 or a pharmaceutically acceptable acid addition salt thereof and a suitable pharmaceutical vehicle.

10. A composition useful for the treatment of susceptible bacterial infections comprising an effective amount of a compound of claim 4 or a pharmaceutically acceptable acid addition salt thereof and a suitable pharmaceutical vehicle.

11. A method for treating infections caused by Mycoplasma species which comprises administering parenterally to an infected or susceptible warm-blooded animal an amount of a composition of claim 7 which is effective against the Mycoplasma species.

12. A method for treating infections caused by Mycoplasma species which comprises administering parenterally to an infected or susceptible warm-blooded animal an amount of a composition of claim 8 which is effective against the Mycoplasma species.

13. A method for treating infections caused by Mycoplasma species which comprises administering parenternally to an infected or susceptible warm-blooded animal an amount of a composition of claim 9 which is effective against the Mycoplasma species.

14. A method for treating infections caused by susceptible gram-positive bacteria which comprises administering to a warm-blooded animal an effective amount of a composition of claim 7.

15. A method for treating infections caused by susceptible gram-positive bacteria which comprises administering to a warm-blooded animal an effective amount of a composition of claim 8.

16. A method for treating infections caused by susceptible gram-positive bacteria which comprises administering to a warm-blooded animal an effective amount of a composition of claim 9.

17. A composition useful for the treatment of susceptible mycoplasmal infections comprising an effective amount of a compound of claim 1 and a suitable pharmaceutical vehicle.

* * * * *